United States Patent [19]

Blomberg

[11] Patent Number: 4,923,980

[45] Date of Patent: May 8, 1990

[54] PROCESS FOR THE MANUFACTURE OF A GEL PRODUCT

[75] Inventor: Arne L. Blomberg, Lund, Sweden

[73] Assignee: BioCarb AB, Sweden

[21] Appl. No.: 268,213

[22] Filed: Nov. 7, 1988

[30] Foreign Application Priority Data

Nov. 10, 1987 [SE] Sweden ................. 8704387

[51] Int. Cl.$^5$ ............... C07H 5/06; C07H 5/04; B01J 20/22
[52] U.S. Cl. ............... 536/55.3; 536/53; 536/18.7; 502/404; 514/23; 424/439; 127/29
[58] Field of Search ............... 127/29, 46.2, 46.3, 127/55; 502/404; 536/121, 18.7, 55.3, 55.2, 30, 45, 52, 53; 514/23; 424/439

[56] References Cited

U.S. PATENT DOCUMENTS 4,029,583  6/1977  Chang et al. ................. 502/404

FOREIGN PATENT DOCUMENTS 0147375   7/1985  European Pat. Off. .
0165800  12/1985  European Pat. Off. .
1391405   4/1975  United Kingdom .

OTHER PUBLICATIONS

Erickson, J. G., "Reactions of Long Chain Amines v. Reactions with Sugars", Journal of American Chemical Society, (May 20, 1955), pp. 2839-2843.

Chemical Abstracts, vol. 95, No. 164863w (1981), "Derivatization of epoxy-activated agarose with various carbohydrates for the preparation of stable and high--capacity affinity absorbants: their use for affinity chromatography of carbohydrate-binding protiens".

Primary Examiner—Chung K. Pak
Attorney, Agent, or Firm—Burns, Doane, Swecker & Mathis

[57] ABSTRACT

A process for the manufacture of a gel product, wherein the reducing sugar is covalently coupled to the matrix of the gel product, characterized in that the sugar, through its reducing end, is coupled to a matrix provided with amino groups to form a glycosyl amine which is then stabilized by acylation to the formation of a glycosyl amide.

11 Claims, No Drawings

PROCESS FOR THE MANUFACTURE OF A GEL PRODUCT

The present invention relates to a process for the manufacture of a gel product, wherein a reducing sugar is covalently bound to the matrix of the gel product.

The present invention has its major and primary utility in so called affinity chromatography, which techniques during the last years have enjoyed an increasing importance, since in principal it is the only technology that enables purification of biological substances based on the biological structure of the substance.

The affinity chromatography is based on chromatography relying upon adsorption, the substance to be purified being reversibly adsorbed on a binder substance which is immobilized on an insoluble carrier of matrix.

During the last years the biological role of carbohydrates has been increasingly subject to scientific research, and it has inter alia been found that carbohydrate structures play an essential role for example as receptors in adherence of bacteria to living tissue, for example mucous membranes. Against this background there is a great interest for techniques that enable coupling of carbohydrate structures onto solid carriers, for example gels.

The present invention has for its object to provide new techniques for coupling a reducing sugar, particularly an oligosaccharide, on to a solid carrier or matrix.

Another object of the invention is to provide such new techniques that do not require prederivatisation of the saccharide before the covalent coupling to the carrier.

Yet another object is to provide techniques enabling easy recovery of the excess of saccharide.

For these and other objects which will be clear from the following disclosure there is provided through the invention a process for the manufacture of a gel product comprising an insoluble carrier or matrix and a reducing sugar covalently coupled thereto. The process according to the invention resides in coupling the sugar via its reducing end to a matrix provided with terminal amino groups to form a glycosylamine, the latter for the purpose of stabilizing same being acylated to the formation of a glycosylamide. This can be diagrammatically illustrated in the following way:

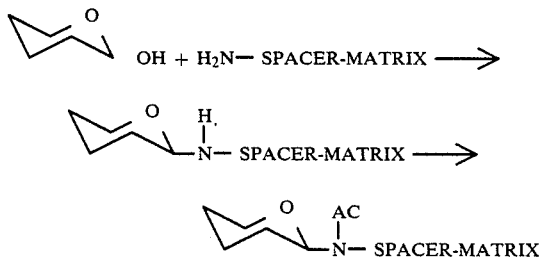

It is particularly preferred to couple the sugar or the ligand to the matrix via a spacer arm provided with a terminal amino group.

The matrix which is part of the product according to the present invention can be of any type as long as it contains amino groups which can be covalently coupled to a reducing sugar acting as a ligand. The matrix may thus be solid, latex-formed (semisolid) or gelatinous to its nature, and it is preferred that the matrix is provided with spacer arms having terminal amino groups. In other respects the character of the matrix is not critical and on the market a number of products are found which are suited for use in connection with application of the invention. As examples of suitable matrices there may be mentioned activated affinity gels of the type Fractogel®, for example Fractogel®TSK AF-AMINO 650 (E. Merck, Westgermany). Other types of affinity gels are Sepharose and Agarose gels, for example AH-Sepharose 4B® and Agarose-Hexylamine, respectively, (the trade name Aghexamine®) (Pharmacia Fine Chemicals, Sweden). All of these affinity gels are supplied by the manufacturers with spacer arms having terminal amino groups coupled thereto. However, the invention is not limited to the just mentioned affinity gels but also others are conceivable, for example silica gels, cellulose gels, BIOGEL®, TRISACRYL®, EUPERGIT C® and others.

Any reducing sugar can be used in the process according to the present invention for coupling to the matrix. Preferred sugars are monomers, dimers or oligomers, but also polysaccharides are conceivable in certain cases. Particularly preferred are, however, saccharides having 1 to 20 monomeric units, particularly up to 10 monomers.

With regard to useful spacer arms their length is not specifically critical, and in certain cases it is conceivable to use terminal amino groups attached directly on to the matrix structure. However, it is preferred if a spacer arm is present that it is not too long, since this can result in the creation of non-specific effects which may reduce the selectivity of the separation. Thus, for example unspecific hydrofobic interactions are not at all desired in affinity chromatography, and for this reason it is preferred that the spacer arm has at most about 25 atoms in its chain. In the affinity gels exemplified above the spacer arm is considerably shorter, often of less than about 10 atoms in its chain. The composition of the chain is not particularly critical, even if it usually is based on a carbon chain. In the gels exemplified above the side chain is constituted by hexamethylene diamine or 3-amino-2-hydroxypropyle.

With regard to the reaction conditions when carrying through the process according to the present invention the following is generally applicable.

In the first step the sugar is coupled via its reducing end to a matrix provided with terminal amino groups to the formation of a glycosylamine. The reaction is carried out in liquid phase using a suitable solvent having a capacity of dissolving the sugar. As examples of such solvent there may be mentioned anhydrous methanol, ethanol, aqueous mixtures thereof or higher alcohols/water mixtures. Also other polar solvents such as DMSO, DMF or the like, can be used. Heating of the solvent results in faster reaction in this first step and is thus preferred in order to reduce the reaction time. The glycosyl amine formed as an intermediate need not be purified from unreacted sugar in the solution. There is, however, the possibility of filtering away this sugar from the gel if desired.

In the second step of the process the glycosyl amine formed under step 1 is stabilized by acylation to the formation of glycosyl amide. The acylation is carried out with an acylating agent containing up to about 10 carbon atoms. In this reaction there is suitably used a reactive derivative of an acid, for example an acid halide, such as acid chloride, or an acid anhydride. The acid is suitably an organic acid, in particular low aliphatic carboxylic acid having at most 6 carbon atoms. A particularly preferred acylation agent is a reactive derivative of acetic acid, for example acetyl chrolide, acetic anhydride or ketene.

The reaction milieu is suitably the same as described above in connection to the first reaction step, i.e. it is particularly preferred to operate in an anhydrous medium. Excess of acylating agent can be removed by filtration, and such excess of acylating agent may often be preferred, since thereby free $NH_2$-groups on the matrix or the spacer arms of the matrix can be blocked so as not to negatively affect a possible biological condition. Excess sugar can be easily recovered after filtering away the finally treated matrix.

The advantages of the techniques of the present invention are several and among such advantages there may be mentioned that the sugar used does not require prederivatisation or the introduction of protective groups, the method is economic since excess of often quite expensive sugar can be recovered.

The invention will in the following be further illustrated by non-limiting examples.

EXAMPLE 1

25 g of suction-dried Fractogel ®TSK AF-AMINO (E. Merck, Westgermany) is washed with methanol several times to remove water. Then, the gel is placed into a bottle provided with a screw cap, and 50 ml of methanol are added thereto. 150 mg (307 μmol) 2'fucosyl lactose (Fucα1-2Galβ1-4Glc) are added to the contents of the bottle. The bottle is placed in a shake water bath at 60° C. and subjected to shaking for 20 hours. The gel is then filtered and washed with methanol.

The gel is then added with 50 ml of an 1:1 (vol/vol) mixture of acetic anhydride and methanol and is allowed to stand under shaking for 22 hours. The gel is then filtered and thoroughly washed with water.

Sugar analysis on 25 mg of the treated gel indicates a substitution rate of 7 μmol 2'fucosyl lactose/g gel (based on the weight of suction-dried gel).

Residual fucosyl lactose can be recovered by rolling and freeze-drying of the filtered mother liquor.

EXAMPLE 2

The pretreatment of the gel and the type of gel were the same as described above in Example 1. The gel is added with 256 mg kitobios GlcNAcβ1-4GlcNAc and subjected to reaction in the same manner as described in Example 1. The gel is then washed with water several times. The combined wash solutions and the original reaction solution are combined and evaporation is carried out to a small volume and then freeze-drying to dryness. 145 mg kitobios can be recovered and is shown by HPLC to be completely pure. The gel is again transfered to methanol and washed and acetylated in the same manner as described in Example 1.

Sugar analysis on the gel indicates a substitution degree of 12 μmol kitobios.

Biological testing of this gel shows that it can bind the lectine "wheat germ agglutinin".

EXAMPLE 3

1 g of a gel of the same type as described in Example 1 is treated in the same manner as in said example. 16 mg of 3'sialyl lactose (Neu5Acα2-3Galβ1-4Glc) is added to the gel. The gel together with the sugar dissolved in methanol is allowed to stand for 48 hours at 40° C. The glycosylamine obtained is then acetylated with acetic anhydride/methanol (1:9 vol/vol). Sugar analysis on the product obtained indicates a substitution degree of about 3 μmol/g.

Residual sugar can be recovered by rolling and freeze-drying and is then shown by HPLC to contain only small quantities of contaminants. Biological testing of this gel shows that it can bind the lectin "wheat germ agglutinin".

EXAMPLE 4

2 g Fractogel of the same type as in Example 1 is transferred to methanol and 17 mg lacto-N-tetraose corresponding to 25 μmol (Galβ1-3GlcNacβ1-3Glc) is added thereto. 3 ml of 70% methanol (30% water) are then added to the mixture. The contents are then shaken at 60° C. for 20 hours. Washing is then carried out with water and acetylation takes place with 10% acetic anhydride/methanol. The sugar analysis indicates a substitution degree of 2 μmol/g.

EXAMPLE 5

5 g of Sepharose gel (AH-Sepharose 4B, hexamethylene diamine spacer, Pharmacia Fine Chemicals, Sweden) are transferred to a flask containing 96% ethanol. To the contents of the flask there are added 47 mg of blood group A-tetrasaccharide, GalNAcα1-3(-Fucα1-2)Galβ1-4Glc and 2 ml of 96% ethanol.

The mixture is allowed to stand at 60° C. for 30 hours, and the gel is then washed with water and acetylated with acetic anhydride/ethanol 1:9. From the washing solution 20 mg of A-tetrasaccharide can be recovered. According to HPLC there are no biproducts.

Sugar analysis on the gel gives a substitution degree of 5–10 μmol/g.

The gel can bind anti-A Ig M and Ig G in serum.

EXAMPLE 6

5 test tubes containing each 1 g of Fractogel of the same type as in Example 1 are each added with 675 mg Melibiose (Galα1-6Glc) and in each tube the gel is mixed with the sugar. The contents of the tubes are then treated as follows, the tubes being designated by letters A–E.

A: 5 ml dimethyl sulfoxide
B: 5 ml methanol
C: 5 ml dimethyl formamide
D: 5 ml dimethyl sulfoxide
E: 5 ml dimethyl formamide Tubes A, B and C are allowed to rest in a cradle at 20° C. for 3 days. Filtration and washing with water is carried out.

Tubes D and E are allowed to stand at 100° C. for 6 hours, and the contents is then filtered off and washed with water. All treated gels are then acetylated using acetic anhydride/methanol 2:1. Sugar analysis on the different gels indicate the following substitution rates:

Gel of tube A: 10 μmol/g
Gel of tube B: 23 μmol/g
Gel of tube C: 15 μmol/g
Gel of tube D: 17 μmol/g
Gel of tube C: 21 μmol/g

EXAMPLE 7

Example 1 is repeated while using propionic anhydride as an acylating agent. The substitution rate obtained by sugar analysis is about 20% lower than that obtained in Example 1.

EXAMPLE 8

Example 1 is repeated with the difference that pure acetic anhydride is added directly to the reaction mixture after heat treatment without preceding filtration and washing. The substitution is in this case about 50% higher than that of Example 1.

I claim:

1. A process for the manufacture of a gel matrix which is covalently coupled with a reducing sugar comprising the steps of coupling the sugar, through its reducing end, to a matrix provided with amino groups to form a glycosyl amine and then stabilizing said glycosyl amine by acylation to form a glycosyl amide.

2. A process according to claim 1 wherein the matrix is solid, semisolid or gelatinous.

3. A process according to claim 1 wherein the acylation is carried out with an acylating agent containing up to about 10 carbon atoms.

4. A process according to claim 3 wherein the acylation agent is a reactive derivative of an organic acid.

5. A process according to claim 4 wherein the acid is a low aliphatic carboxylic acid.

6. A process according to claim 4, wherein said reactive derivative of the organic acid is a derivative of acetic acid.

7. A process according to claim 1 wherein the sugar is an oligosaccharide.

8. A process according to claim 1 wherein the sugar is a saccharide having 1 to 20 monomeric units.

9. A process according to claim 2 wherein the acylation is carried out with an acylating agent containing up to about 10 carbon atoms.

10. A process according to claim 2 wherein the sugar is an oligosaccharide.

11. A process according to claim 6 wherein said derivative of acetic acid is acetic anhydride.

* * * * *